(12) United States Patent
Gianotti

(10) Patent No.: US 7,331,990 B2
(45) Date of Patent: *Feb. 19, 2008

(54) STENTS WITH PROXIMAL AND DISTAL END ELEVATIONS

(75) Inventor: Marc Gianotti, Wiesendangen (CH)

(73) Assignee: Schneider (Europe) GmbH, Bulach (CH)

( * ) Notice: Subject to any disclaimer, the term of this patent is extended or adjusted under 35 U.S.C. 154(b) by 0 days.

This patent is subject to a terminal disclaimer.

(21) Appl. No.: 10/674,729

(22) Filed: Sep. 30, 2003

(65) Prior Publication Data

US 2004/0098077 A1    May 20, 2004

Related U.S. Application Data

(62) Division of application No. 09/874,609, filed on Jun. 5, 2001, now Pat. No. 6,652,577, which is a division of application No. 09/431,988, filed on Nov. 2, 1999, now Pat. No. 6,240,978, which is a division of application No. 08/993,033, filed on Dec. 18, 1997, now Pat. No. 5,993,483.

(30) Foreign Application Priority Data

Jul. 17, 1997    (EP) .................................. 97202152

(51) Int. Cl.
*A61F 2/06* (2006.01)
(52) U.S. Cl. .................................................. 623/1.22
(58) Field of Classification Search ............... 623/1.22, 623/1.16, 1.2, 1.3, 1.28, 1.51
See application file for complete search history.

(56) References Cited

U.S. PATENT DOCUMENTS

| 4,553,545 | A | 11/1985 | Maass et al. ............... 128/341 |
|---|---|---|---|
| 4,655,771 | A | 4/1987 | Wallsten .......................... 623/1 |
| 4,732,152 | A | 3/1988 | Wallsten et al. ............. 128/343 |
| 4,760,849 | A | 8/1988 | Kropf ........................... 128/341 |
| 4,770,664 | A | 9/1988 | Gogolewski .................. 623/66 |
| 4,771,773 | A | 9/1988 | Kropf ........................... 128/303 |
| 4,848,343 | A | 7/1989 | Wallsten et al. ............. 128/343 |
| 4,850,999 | A | 7/1989 | Planck ............................ 623/1 |
| 4,875,480 | A | 10/1989 | Imbert ......................... 128/343 |
| 4,954,126 | A | 9/1990 | Wallsten ....................... 600/36 |
| 4,990,151 | A | 2/1991 | Wallsten ...................... 606/108 |
| 5,019,090 | A | 5/1991 | Pinchuk ....................... 606/194 |
| 5,026,377 | A | 6/1991 | Burton et al. ............... 606/108 |
| 5,061,275 | A | 10/1991 | Wallsten et al. ................ 623/1 |
| 5,071,407 | A | 12/1991 | Termin et al. .............. 604/104 |
| 5,092,877 | A | 3/1992 | Pinchuk .......................... 623/1 |
| 5,147,385 | A | 9/1992 | Beck et al. ..................... 623/1 |
| 5,201,757 | A | 4/1993 | Heyn et al. .................. 606/198 |
| 5,221,261 | A | 6/1993 | Termin et al. .............. 604/104 |

(Continued)

FOREIGN PATENT DOCUMENTS

EP    0775471 A1    5/1997

(Continued)

*Primary Examiner*—Bruce Snow
(74) *Attorney, Agent, or Firm*—Hoffmann & Baron, LLP

(57) ABSTRACT

A prosthetic stent with a tubular wall having local inwardly or outwardly formed elevations. Stents having such elevations have a higher mechanical stability if bent according to the curvature of the body vessels to be supported or repaired. Also a method for manufacturing a stent with such elevations is described.

5 Claims, 4 Drawing Sheets

U.S. PATENT DOCUMENTS

| | | | |
|---|---|---|---|
| 5,226,913 A | 7/1993 | Pinchuk | 623/1 |
| 5,356,423 A | 10/1994 | Tihon et al. | 606/194 |
| 5,378,239 A | 1/1995 | Termin et al. | 604/104 |
| 5,405,380 A | 4/1995 | Gianotti et al. | 623/1 |
| 5,464,408 A | 11/1995 | Duc | 606/108 |
| 5,484,444 A | 1/1996 | Braunschweiler et al. | 606/108 |
| 5,496,277 A | 3/1996 | Termin et al. | 604/104 |
| 5,507,767 A | 4/1996 | Maeda et al. | 606/198 |
| 5,534,287 A | 7/1996 | Lukic | 427/2.25 |
| 5,554,181 A | 9/1996 | Das | 623/1 |
| 5,556,426 A | 9/1996 | Popadiuk et al. | 623/1 |
| 5,575,818 A | 11/1996 | Pinchuk | 623/1 |
| 5,591,172 A | 1/1997 | Bachmann et al. | 606/108 |
| 5,591,226 A | 1/1997 | Trerotola et al. | 623/1 |
| 5,607,466 A | 3/1997 | Imbert et al. | 623/1 |
| 5,609,624 A | 3/1997 | Kalis | 623/1 |
| 5,626,602 A | 5/1997 | Gianotti et al. | 606/198 |
| 5,628,787 A | 5/1997 | Mayer | 623/1 |
| 5,628,788 A | 5/1997 | Pinchuk | 623/1 |
| 5,630,840 A | 5/1997 | Mayer | 623/1 |
| 5,645,559 A | 7/1997 | Hachtman et al. | 606/198 |
| 5,662,703 A | 9/1997 | Yurek et al. | 623/1 |
| 5,667,486 A | 9/1997 | Mikulich et al. | 604/8 |
| 5,679,470 A | 10/1997 | Mayer | 428/662 |
| 5,709,713 A * | 1/1998 | Evans et al. | 623/1.53 |
| 5,725,547 A | 3/1998 | Chuter | 606/194 |
| 5,817,126 A | 10/1998 | Imran | 606/198 |
| 5,836,964 A | 11/1998 | Richter et al. | 606/194 |
| 5,879,342 A | 3/1999 | Kelley | 604/282 |
| 5,891,191 A | 4/1999 | Stinson | 623/1 |
| 5,993,483 A | 11/1999 | Gianotti | 623/1 |
| 6,027,529 A | 2/2000 | Roychowdhury et al. | 623/1 |
| 6,231,598 B1 | 5/2001 | Berry et al. | 623/1.15 |
| 6,302,907 B1 | 10/2001 | Hijlkema | 623/1.16 |
| 6,551,352 B2 | 4/2003 | Clerc | 623/1.2 |
| 6,585,758 B1 | 7/2003 | Chouinard et al. | 623/1.16 |
| 6,596,191 B2 | 7/2003 | Sakamoto et al. | 252/188.28 |
| 6,613,072 B2 | 9/2003 | Lau et al. | 623/1.11 |
| 6,652,577 B2 | 11/2003 | Gianotti | 623/1.22 |
| 2001/0010015 A1 | 7/2001 | Hijlkema | 623/1.16 |
| 2002/0040236 A1 | 4/2002 | Lau et al. | 623/1.12 |
| 2002/0165597 A1 | 11/2002 | Clerc | 623/1.2 |
| 2003/0065381 A1 | 4/2003 | Solar et al. | 623/1.15 |
| 2003/0130718 A1 | 7/2003 | Palmas et al. | 623/1.12 |
| 2003/0135265 A1 | 7/2003 | Stinson | 623/1.16 |

FOREIGN PATENT DOCUMENTS

| | | |
|---|---|---|
| EP | 0621015 B1 | 3/1998 |
| WO | WO9412136 | 6/1994 |
| WO | WO9625124 | 8/1996 |
| WO | WO9629955 | 10/1996 |

* cited by examiner

STENTS WITH PROXIMAL AND DISTAL END ELEVATIONS

This is a divisional of prior application Ser. No. 09/874,609, (now U.S. Pat. No. 6,652,577), filed Jun. 5, 2001 as a divisional of application Ser. No. 09/431,988 (now U.S. Pat. No. 6,240,978), filed Nov. 2, 1999 as a divisional of application Ser. No. 08/993,033 (now U.S. Pat. No. 5,993,483), filed Dec. 18, 1997.

BACKGROUND OF THE INVENTION

This application claims priority under 35 U.S.C. § 119 of European Patent Application No. 97202152.1, filed in the European Patent Office on Jul. 17, 1997.

The present invention relates to a stent for use in a body passageway, comprising a flexible self-expanding braided tubular wall being composed of helically wound wires and having proximal and distal ends. The invention also relates to a method for manufacturing such a stent.

A stent of the type as mentioned in the introduction is described for example in U.S. Pat. No. 4,655,771. The tubular wall is composed of several flexible thread elements each of which extends along a helix with the center line of the tubular wall as a common axis. The thread elements are arranged in two groups of opposite directions of winding crossing each other in a way to form a braided configuration. This is to impart to the tubular body the necessary stability for supporting a vessel. The diameter of the tubular wall can be changed by axial movement of the ends relative to each other. The stent is transluminally inserted into position in its radially compressed state and then subjected to expansion staying in place by a permanent pressure against the inner wall of the body passageway. The stability of the tubular body depends in general from the number of the thread elements, their diameter and material and from the braiding angle of the thread elements at their crossings. It is preferred to have the axially directed braiding angle being obtuse, i.e. larger than 90°, in order to obtain a large force in radial directions. But the braiding angle also influences the shortening of the stent, which is the reduction of the scent length upon conversion from its compressed to its expanded state. At a given diameter expansion the stent shortens less at braiding angles smaller than around 120° than at larger angles.

In the following stents with a braiding angle larger than about 120° are referred to as "normal-shortening" whereas stents having a braiding angle of less than about 120° are referred to as "less-shortening." It is an advantage of less-shortening stents that they can be placed more accurately because the practitioner can better estimate the final positions of the stent ends after expansion. The less-shortening feature comes also to fruition when the stent is implanted in a moving hollow organ in which the stent is repeatedly radially compressed, such as in the esophagus, in the trachea or in a pulsating blood vessel. In those cases the reduced shortening of the stent is less traumatic for the inner wall of the hollow organ since the stent ends perform smaller axial movements than normal-shortening stents do. For the aforesaid reasons less-shortening stents are preferably implanted in ostium regions, for example in the aorta next to the entries into the renal arteries or in side branches. Exact placement capability and less axial movement of the stent ends reduce the risk of unwanted perturbation or obstruction of the blood flow by stent ends projecting into the ostium.

However, stents of the less-shortening type comprise smaller hoop strength compared to normal-shortening prostheses due to their smaller braiding angle. A consequence of the lower radial force is a reduction of the self-fixation characteristics with the risk of a local axial displacement of the stent within the body passageway. Moreover, the stent is not stable enough to resist flattening if it is implanted in arched vessels. This means that a more or less strong deformation of the stent cross-section deviating from its original circular shape can partially close the stent.

In EP-A-O 775 471 an improved stent is disclosed comprising a flexible self-expanding braided tubular wall having a proximal segment of smaller diameter and a distal segment of larger diameter and in-between an intermediate segment forming a truncated cone. A covering layer is arranged within the tubular wall. Although the document does not disclose any specific braiding angles the proximal segment will have a similar braiding angle as the above described less-shortening stent and the distal segment will have a larger braiding angle. The different geometry can be derived from the manufacturing methods as described in the document. The large-diameter segment serves as a migration anchor while the less-shortening segment with smaller diameter makes an easier and safer way through curves or at the end of for example a food pipe. But the less-shortening stent segment still has not sufficient shape stability for use in curved areas of body vessels. The cross-section of this segment may be deformed elliptically if bended in curved body vessels as it will occur generally for less-shortening stents. Moreover, because of the conical shape such a stent can be used only at particular areas, such as in food pipes. In addition, it is to be said that the used manufacturing methods are quite expensive.

All documents cited herein, including the foregoing, are incorporated herein by reference in their entireties for all purposes.

SUMMARY OF THE INVENTION

It is therefore an object of the present invention to improve a less-shortening stent such that it can be used universally, and more specifically in moving and/or in curved body passageways avoiding migration and flattening deformation thereof. A further object of the invention is to provide a stent which can be manufactured easier.

The term "elevation" has the meaning of an impression or bulge of the stent wall as well in the negative as in the positive sense, i.e. extending inwardly or outwardly of the tubular stent wall. Accordingly, the tubular wall has at least a local inwardly and/or outwardly formed elevation, whereby the wires are plastically deformed in a way that the number of degrees of freedom for their movement within the braiding is reduced. This means that the mesh cells defined by the braided wires are "frozen" by a reduced capability of the wires to rotate and shift relative to each other at their crossing points. The braided tubular wall retains its less-shortening feature and becomes more stable against radial deformation. A further advantage of the formed elevations is the possibility to make a short stent of the type mentioned in the introduction. Such stents are usually cut from the braiding blank and comprise an unwanted conical shape due to a memory effect from the braiding process. This shape can be converted into a cylindrical tube and conserved by forming elevations on the stent wall.

Where the elevations are distributed regularly over the tubular wall, the stent will be anchored firmly with the tissue of the body vessel without damaging. The homogeneity of the elevation distribution is for example preferred if the stent is to be implanted in a curved area of a body passageway.

More dense distribution of the elevations at the proximal and distal ends of the stent will provide higher stability at these areas for better anchoring thereof with the tissue of the body vessel. This embodiment is preferred if the stent is to be implanted in ostium positions for a safe fixation of the stent ends in order to prevent migration of the stent and disturbing for example the blood flow into a side branch through this ostium. Another preferred application of such a stent is the support of a vessel having a hard plaque stenosis whereby the stent comprises a higher density of elevations in the stenotic region.

In a preferred embodiment of the invention the elevations are formed outwardly so that they can serve as an anchor against stent migration by engaging into the inner vessel wall to be supported. Moreover, the deployment of such a stent with delivery devices as known in the art is enhanced since the retraction of the outer sheath is easier. This results from a reduced friction between the inside of the delivery sheath and the radially outwardly pressing stent touching the sheath only at the elevations.

In another preferred embodiment of the present invention the local elevations have an elongate shape which makes the manufacturing of such stents very easy by using wires to emboss the tubular wall. The elevations may have an arched cross-sectional shape. Preferably the height of the elevations are approximately one to two times the wire diameter of the braid.

These embossments or elevations can be formed in patterns helically on the tubular wall, where in a preferred embodiment the helical elevation pattern has a different pitch than the wires of the braid in order to deform as many wires as possible. The elevations may also be formed annularly or in an axial direction on the tubular wall depending on the desired effect. Where the elevations are placed annularly the stent wall comprises an improved radial stability, whereas elevations in axial directions impart to the stent a higher longitudinal stability which is especially useful for implantation in the airways.

The manufacturing method according to the present invention is determined by the steps of forming an elongate mandrel having at least one local outwardly bound elevation, forming an elongated tubular braid of spring steel having proximal and distal ends and an inner diameter commensurate with the diameter of the mandrel, engaging said tubular braid over said mandrel, heating the tubular braid on the mandrel, cooling the tubular braid and disengaging the braid from the mandrel. Preferably previous to the disengaging step the braid will be compressed in the axial direction.

In sum the present invention relates to a stent for use in a body passageway. A flexible self-expanding braided tubular wall is composed of helically wound wires and has proximal and distal ends, wherein the tubular wall has at least a local inwardly and/or outwardly formed elevation. The local elevations may be distributed regularly over the tubular wall and distributed more densely at the proximal and distal ends. The local elevations of the stent may be formed outwardly and may have an elongated shape. The stent elevations may have an arched cross-sectional shape and/or a height of approximately one to two times of the diameter of the wires. The elevations may be formed helically on the tubular wall. The helical elevation may have a different pitch than the wires of the braid. The elevation may be formed annularly on the tubular wall or formed in an axial direction on the tubular wall.

The invention further relates to a method for manufacturing a stent by forming or providing an elongated mandrel having at least one local outwardly bound elevation; forming or providing an elongated tubular braid of spring steel having proximal and distal ends and an inner diameter commensurate with the diameter of the mandrel; engaging the tubular braid over the mandrel; heating the tubular braid over the mandrel; cooling the tubular braid; and disengaging the braid from the mandrel. Prior to disengaging the braid from the mandrel, the braid may be compressed in an axial direction. The steps of heating the tubular braid over the mandrel and cooling the tubular braid may be performed under vacuum condition.

BRIEF DESCRIPTION OF THE DRAWINGS

These and other objects, features and advantages of the present invention will become readily apparent from the subsequent description, wherein the invention will be explained in further details with reference to the accompanying drawings which show, diagrammatically and by way of example only, preferred but still illustrative embodiments of the invention.

In the following description of the drawings the same reference numbers have been used for all figures if not mentioned otherwise.

DETAILED DESCRIPTION OF THE INVENTION

Figure 1:
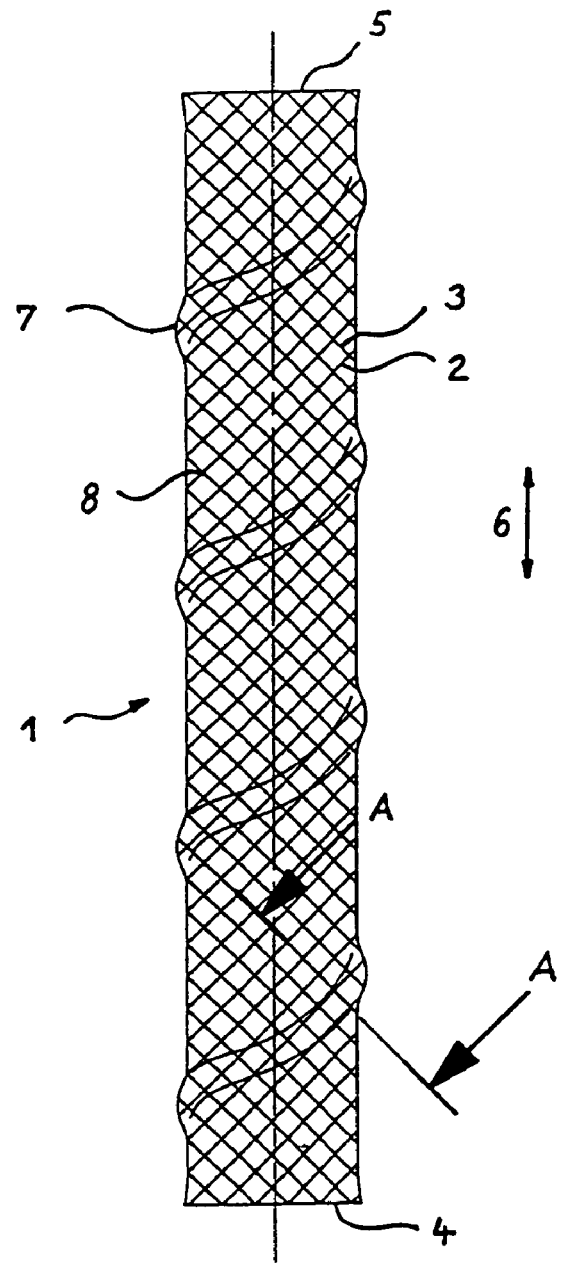
FIG. 1 shows a stent with a helical elevation in side view.

The stent depicted in FIG. 1 comprises a flexible self-expanding braided tubular wall 1 which is composed of a first plurality of parallel spring stainless steel wires 2 helically wound in a first direction crossing a second plurality of parallel spring stainless steel wires 3 helically wound in a second direction opposite to the first one. The braided structure assures contraction of the stent in the radial direction when the proximal and distal ends 4 and 5 of the stent are pulled away from one another as exemplified by arrows 6, and self-expansion of the stent in the radial direction when the pull according to arrows 6 is released. This configuration is well known in the art and needs no further explanation. Of course, other known braidings or patterns providing the same effect may be used.

Figure 2:
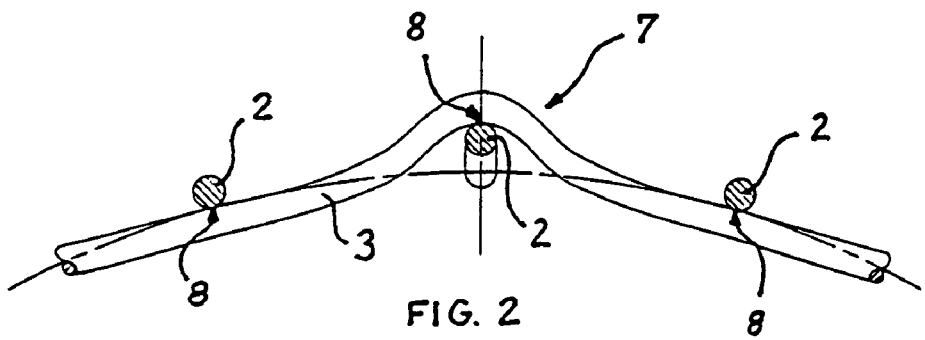
FIG. 2 shows a cross-sectional view according to line A-A in FIG. 1.

The tubular wall 1 of the stent having a helical pattern of elevations 7 which is outwardly formed and has an angle of gradient or pitch slightly smaller than the angle of gradient or pitch of the steel wires 2 shown in the same winding direction. The elevations 7 have an elongate and arched cross-sectional shape. The height of the elevations 7 over the tubular wall 1 is about once or twice the diameter of the wires 2 or 3 of the braided configuration. The wires 2 and 3 may be made of a metallic material, e.g. stainless steel, which may be filled with a radiopaque core, or made of a thermoplastic polymer, such as polyesters, polyurethanes, polycarbonates, polysulphides, polypropylene, polyethylene or polysulphonates. Normally the diameter of the wires 2 and 3 lie within the range 0.01 to 0.5 mms. The helical elevation 7 provides a greater stability of the meshes of the braided tubular wall 1, i.e. the parallel wires 2 and the parallel wires 3 will be prevented from moving apart at the crossing points 8. Especially in the cross-sectional view of FIG. 2 it can be seen that wires 2 and 3 have been deformed locally in a tubular shape. The elevation pattern is normally distributed in a regular manner over the tubular wall 1. Therefore a specific wire 2 or 3 will have several elevation areas over its whole length within the tubular wall 1 and a much greater stability of the wires 2 and 3 within the braid will be obtained. The elevation is further smooth curved, i.e. having a continuous smoothly inclining and declining curvature with the effect that the spring activity of the wires 2 and 3 will be reduced in the areas of the elevations. On the other hand the braiding angle between the wires 2 and 3 will be enlarged locally in the area of the elevations which will additionally enhance the mechanical stability of the tubular wall 1. In fact, the meshes are immobilized or "frozen" at the crossing points of the wires 2 and 3 in the area of the elevation. By the frozen meshes the tubular wall 1 will obtain an enlarged shape stability which will resist the deforming forces of the body vessel. The elevation 7 will also reduce the tendency of the wires 2 and 3 to debraid at the proximal and distal ends 4 and 5 of the tubular wall 1. Thus the aforementioned stent will have a greater form or shape stability if the tubular wall 1 will be bent in blood vessels with a strong curvature, i.e. the circular cross-section of the tubular wall 1 will be retained and not deformed to an elliptical one as can be observed with less-shortening stents.

Figure 3:
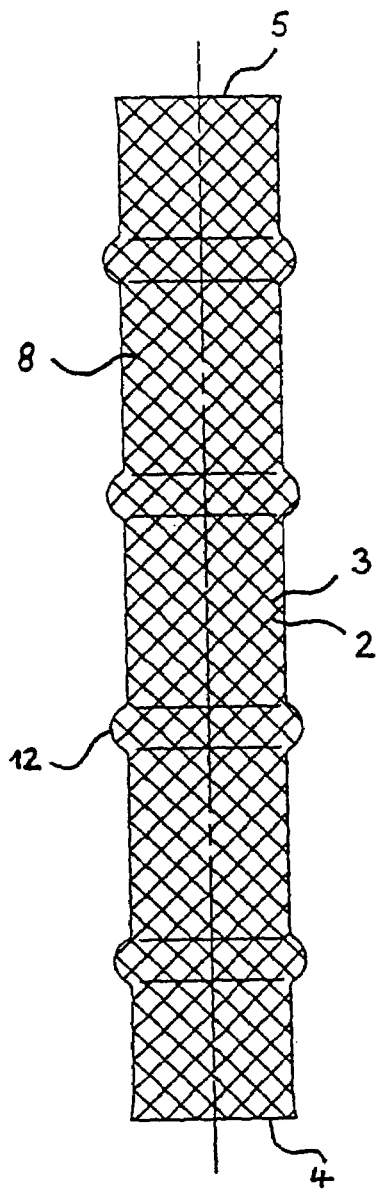
FIG. 3 shows a stent with a plurality of radial elevations in side view.

Another possibility of providing elevations for stents according to the present invention is shown in FIG. 3, where the stent having annular pattern of outwardly formed elevations 12 which, are equidistant and parallel to each other. Here also the stability of the stent has been improved over the well-known stents. If an annular pattern of elevations 12 will be provided near the proximal and distal ends 4 and 5 the tendency of debraiding of the wires 2 and 3 can be reduced further.

Figure 4:
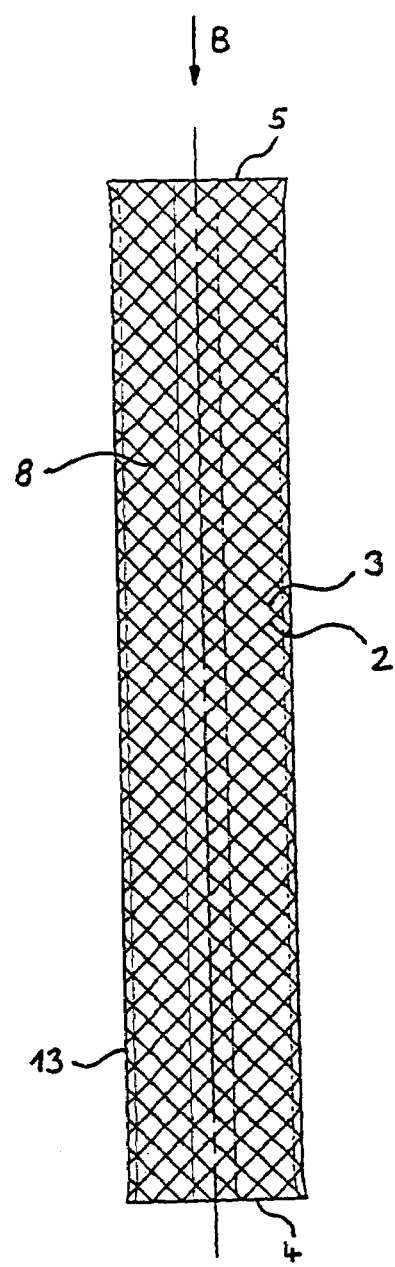
FIG. 4 shows a stent with a plurality of axial elevations in side view.
Figure 5:
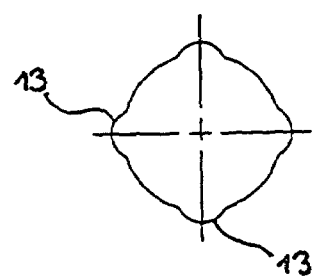
FIG. 5 shows the stent of FIG. 4 in front view according to arrow B.

In FIG. 4 another example of a stent according to the invention is shown, wherein outwardly formed elevations 13 are provided in an axial direction on the tubular wall 1, which elevations 13 are also equidistant and parallel to each other. The front view of FIG. 5 shows that these elevations are also smoothly curved as in the previous examples. Since the wires 2 and 3 are intertwined with a relatively dense mesh the four patterns of elevations 13 as depicted in this example are sufficient to prevent debraiding at the proximal and distal ends 4 and 5 of the stent.

Although the elevations 7, 12 and 13 in the examples of FIGS. 1, 3 and 4 are formed outwardly on the tubular wall 1, they may also be formed inwardly on the tubular wall 1 or possibly provided in combination of outwardly and inwardly formed elevations.

Figure 6:
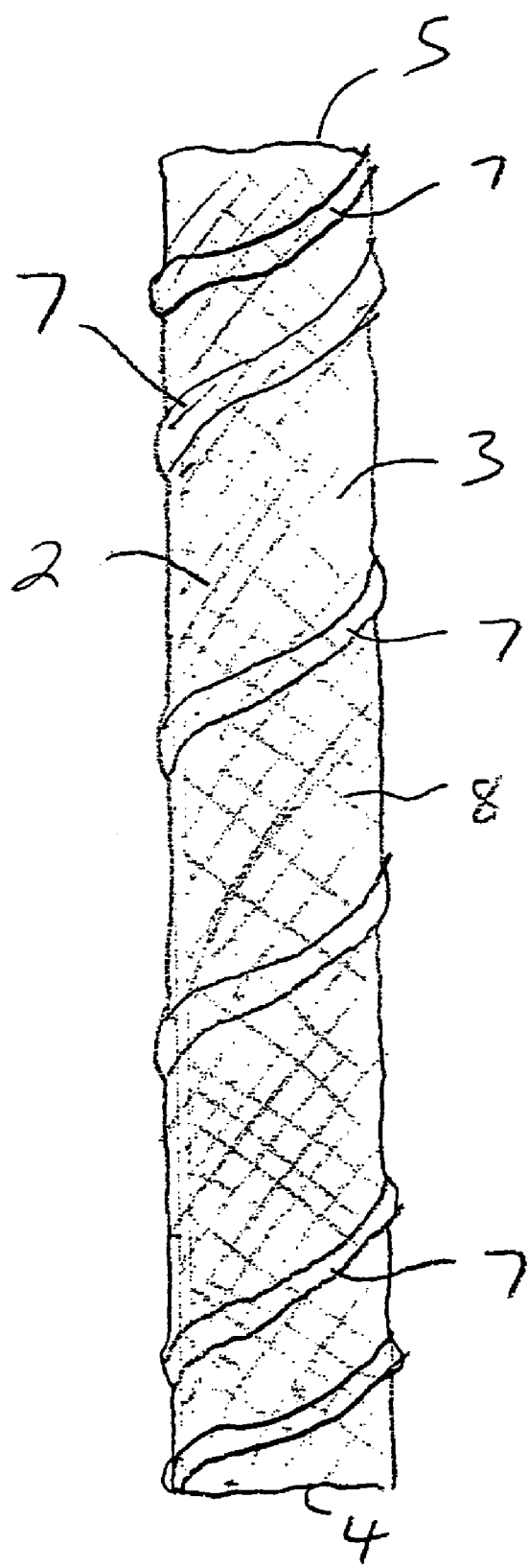
FIG. 6 shows a stent similar to that in FIG. 1, but with increased densities of elevations at its ends.
Figure 7:
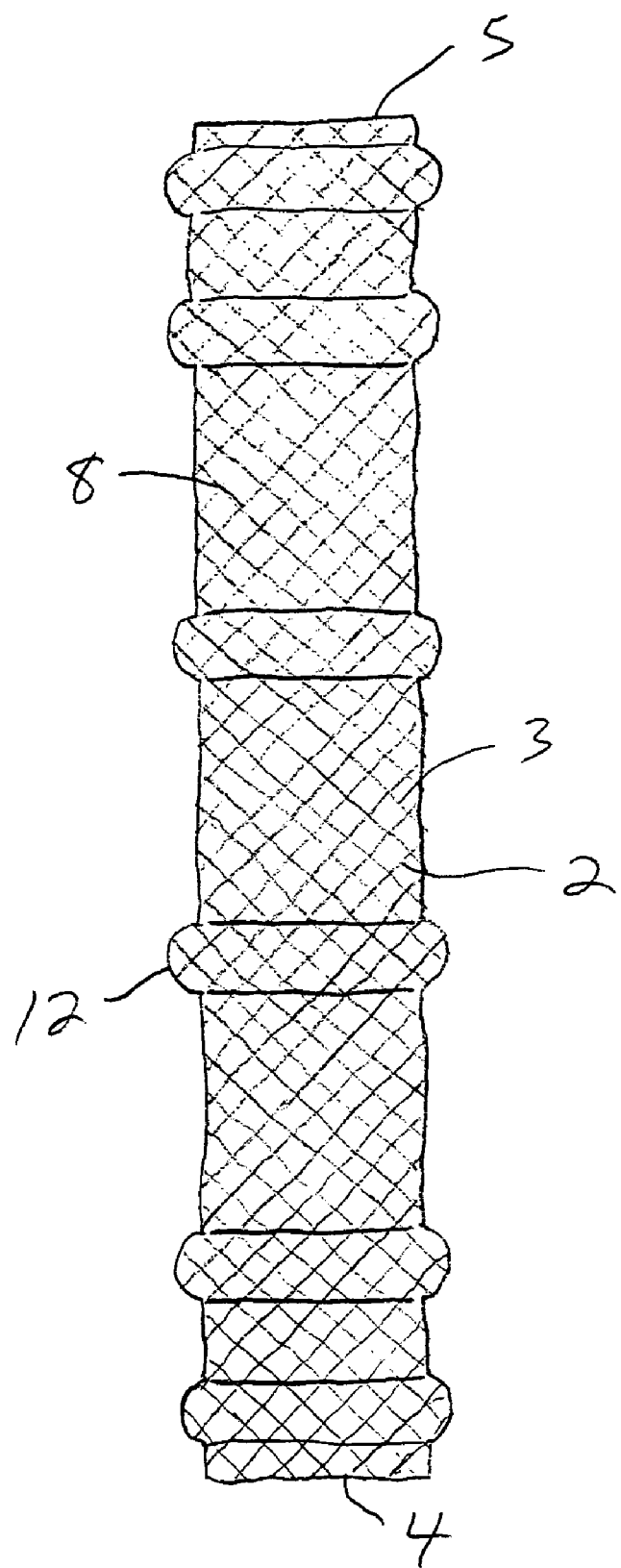
FIG. 7 shows a stent similar to that in FIG. 3, but with increased densities of elevations at its ends.

As mentioned previously, more dense distributions of elevations at the proximal and distal ends of the stent will provide higher stability at these areas for better anchoring of the stent with the tissue of the body vessel. Also, in connection with FIG. 3 it is noted above that an annular elevation pattern 12 near the proximal and distal ends 4 and 5 can reduce the debraiding tendency. FIG. 6 shows a stent of the type shown in FIG. 1, but with increased densities of elevations at the proximal and distal ends. FIG. 7 shows a stent of the type shown in FIG. 3, but with annular elevation patterns near the proximal and distal ends 4 and 5.

The manufacturing of the aforementioned stents is as follows:

Firstly the stent will be produced in the known manner, i.e. the wires 2 and 3 will be intertwined with a predetermined braiding angle and with a predetermined mesh size dependent from the wire cross-section. The braiding angle of the so formed stent will normally be between 100° and 120°. Thereafter the stent will be pushed over a cylindrical mandrel with a regular pattern of outwardly formed elevations like the helical shape of wires provided on the surface of the mandrel as will be used to form a stent according to FIG. 1. The mandrel with the stent will then be heated up to process temperature, kept under process temperature for a certain period of time, and cooled down afterwards. The heating and cooling procedure is carried out under vacuum condition. In the case of stainless steel wires the thermal treatment may take up to sixteen hours, whereby the process temperature of 550° C. is maintained for about two hours. Then the stent will be pulled from the mandrel. In cases where the patterns of elevations are not axially directed as for the stent depicted in FIG. 4, the tubular wall 1 may be compressed in order to enlarge the diameter thereof for an easier disengagement. In case of the helical pattern of the elevations the stent may also be unscrewed from the mandrel.

Although other patterns of elevations may also be used for the stents according to the invention the shown patterns are preferred since they guarantee a smooth outer surface of the tubular wall 1 which is especially important for stents to be used at delicate areas such as blood vessels in order not to damage the tissue. The helical shape and the annular shape of the pattern of elevations are preferred for stents used at the junction between the esophagus and the stomach as these will prevent much better the migration of the stent as in case of the axial pattern of elevations. In particular the elevations may also be formed inwardly instead of outwardly as shown and described above, i.e. the tubular stent wall having depressions. This may be advantageous if the body vessel to be repaired needs more support and a larger contact area with the stent.

Stents according to the present invention have a further advantage in that they can be handled easier in the flexible shaft of the positioning instrument since the friction between the stent and the inner wall thereof will be reduced. This applies more for the outwardly formed elevations as for the ones inwardly formed. But in both cases the friction will be reduced in comparison to conventional stents. Thus repositioning of stents with elevations as shown before has been improved also.

The above-described embodiments of the invention are merely descriptive of its principles and are not to be considered limiting. Further modifications of the invention herein disclosed will occur to those skilled in the respective arts and all such modifications are deemed to be within the scope of the invention as defined by the following claims.

I claim:

1. A body insertable prosthesis, including:
   a flexible self-expanding tubular mesh wall comprising a plurality of elongate wire segments cooperating to form multiple crossing points at which different ones of the elongate wire segments cross each other;
   wherein at a number of selected crossing points, said number being less than the total number of crossing points, pairs of the elongate wire segments crossing one another are shaped to form respective first and second elevations extended in the same direction radially away from the tubular mesh wall; and wherein the elevations are arranged in a helical elevation pattern on the tubular mesh wall.

2. The prosthesis of claim 1 wherein:
said elevations extend radially outwardly from the braided tubular wall.

3. The prosthesis of claim 1 wherein:
the plurality of elongate wire segments include a first wire segment wound helically at a first pitch and a second wire segment wound helically at a second pitch different from the first pitch, and the at least one elevation pattern has a third pitch different from the first pitch and different from the second pitch.

4. The prosthesis of claim 1 wherein:
the tubular mesh wall comprises at least one wire wound to form said crossing points, and said elongate wire segments comprise different length-portions of the at least one wire.

5. A stent insertable into the body passageway, including:
a flexible self-expanding braided tubular wall comprising at least one first wire helically wound at a substantially constant first pitch and at least one second wire helically wound at a substantially constant second pitch different from the first pitch whereby the first and second wires cooperate to form multiple crossing points of the at least one first wire and the at least one second wire;

wherein at selected crossing points, each of the first wire and the second wire is shaped to form an elevation extended away from the braided tubular wall in a selected direction radially of the braided tubular wall; and wherein said elevations are arranged in at least one elevation pattern on the braided tubular wall, and the at least one elevation pattern has a third pitch different from the first pitch and different from the second pitch;

wherein the elevations are arranged in a helical elevation pattern on the braided tubular wall.

* * * * *